US00PP25625P2

(12) United States Plant Patent
Delabroye

(10) Patent No.: US PP25,625 P2
(45) Date of Patent: Jun. 16, 2015

(54) ***HEUCHERA* PLANT NAMED 'VULCANO'**

(50) Latin Name: *Heuchera*
Varietal Denomination: Vulcano

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 103 days.

(21) Appl. No.: 13/694,477

(22) Filed: Dec. 5, 2012

(51) Int. Cl.
*A01H 5/12* (2006.01)

(52) U.S. Cl.
USPC ..... Plt./440

(58) Field of Classification Search
USPC ..... Plt./440
CPC ..... A01H 5/02; A01H 5/12; A01H 5/00; A01H 5/025
See application file for complete search history.

(56) References Cited

PUBLICATIONS

Loader (Heucheraholics the blog Jun. 22, 2011, retrieved from the Internet at <http://heucheraholics.blogspot.com/2011/06/new-heucheras-heucherellas-and.html> 3 pp.).*

UPOV Pluto Plant Variety Database 20140709 for *Heuchera* 'Vulcano' retrieved on Jul. 17, 2014, retrieved from the Internet at <http://www.upov.int/pluto/en/index.jsp> one page.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Vulcano', characterized by its foliage with leaves that are light brownish red in color with silver mottling and light brownish red margins on the upper surface and purple-red on the lower surface, its dark pink flowers on dark brown-red flowering stems, its vigorous growth habit, and its tolerance to heat and humidity.

2 Drawing Sheets

SUMMARY OF THE INVENTION

The following traits have been repeatedly observed and represent the characteristics of the new cultivar. These attributes in combination distinguish 'Vulcano' as a new and unique cultivar of *Heuchera*.

1. 'Vulcano' exhibits unique foliage with leaves that are light brownish red in color with silver mottling and light brownish red margins on the upper surface and purple-red on the lower surface.
2. 'Vulcano' exhibits dark pink flowers on dark brown-red flowering stems.
3. 'Vulcano' exhibits a vigorous growth habit.
4. 'Vulcano' exhibits a tolerance to heat and humidity.

'Vulcano' is a unique *Heuchera* with foliage coloration that is unknown to exist in other cultivars of *Heuchera* known to the Inventor. 'Vulcano' can be most closely compared to the cultivars: 'Circus', 'Crème Brulee' (not patented) and Brown Sugar' for its similarity in foliage coloration and in having *Heuchera×villosa* in its parentage. 'Brown Sugar' differs from 'Vulcano' in having foliage that is brown in color with silver mottling and in being more floriferous with lighter pink flowers. 'Crème Brulee' differs from 'Vulcano' in having more ruffled foliage that is peachy orange in summer and becomes brown in cold temperatures, and in having creamy white flowers. 'Circus' differs from 'Vulcano' in having leaves that are more peach in color reddish veining in spring and fall and lime green with a slight silver overlay and red veining in summer.

BRIEF DESCRIPTION OF THE DRAWING

The accompanying colored photographs illustrate the overall appearance and distinct characteristics of the new

*Heuchera*. The photographs were taken of a plant two years in age as grown outdoors in a 10-liter container in The Netherlands.

Figure 1:
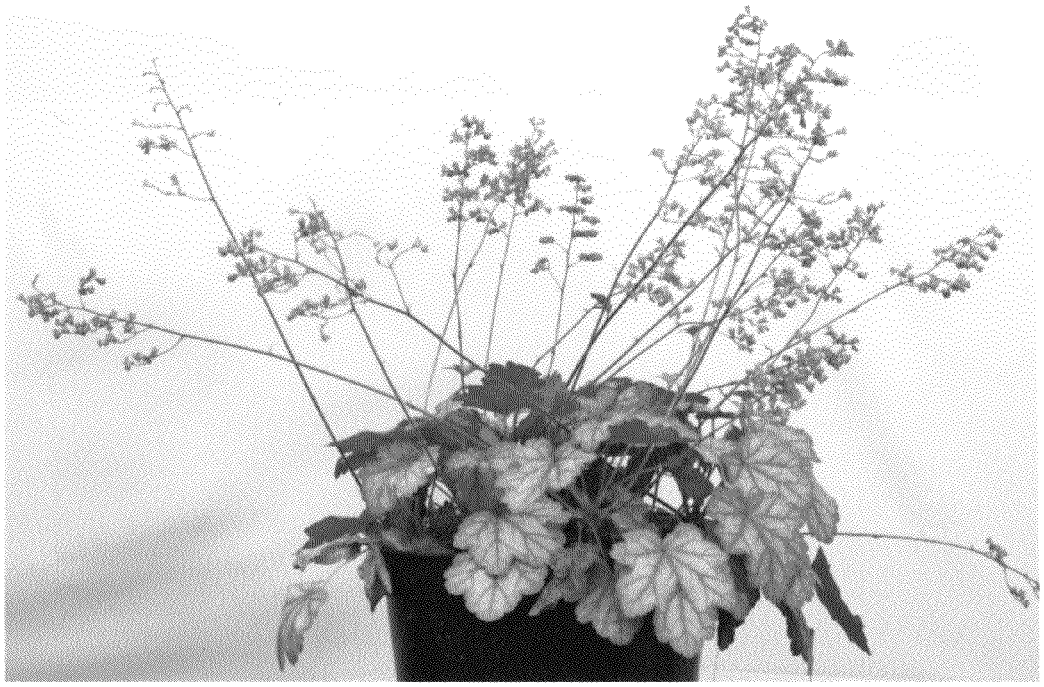

The photograph in FIG. 1 provides a view of the plant habit of 'Vulcano' in bloom.

Figure 2:
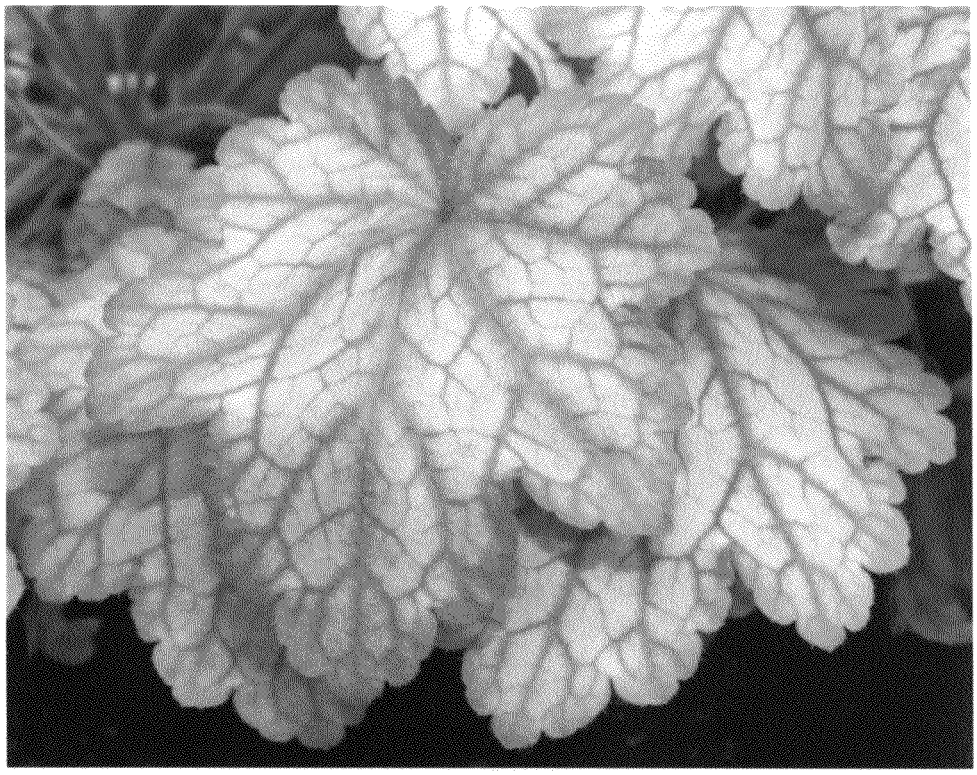

The photograph in FIG. 2 provides a close-up view of the foliage of 'Vulcano'.

Figure 3:
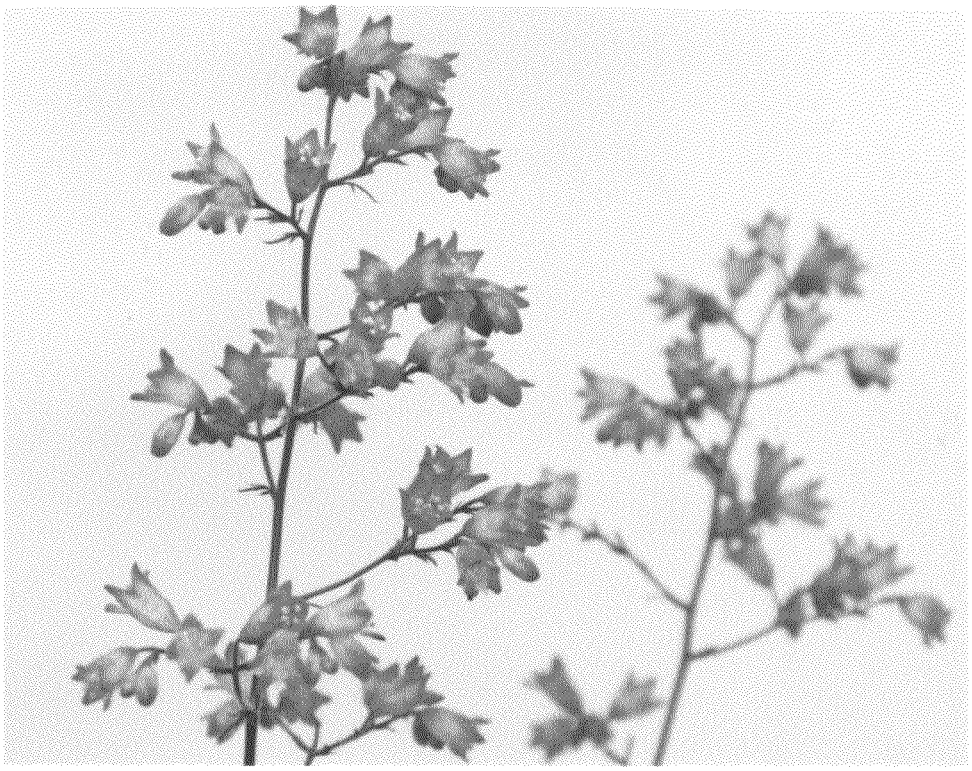

The photograph in FIG. 3 provides a close-up view of the flowers of 'Vulcano'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year old plants of the new cultivar as grown outdoors in 10-liter containers in The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early spring-spring in The Netherlands.

*Plant type.*—Herbaceous perennial.

*Plant habit.*—Clump-forming, mounded foliage.

*Height and spread.*—Average of 17.2 cm in height from soil to top of leaves, 47.5 cm from soil to top of inflorescences, and an average of 82 cm in width.

*Hardiness.*—At least in U.S.D.A. Zones 3 to 8.

*Diseases and pests.*—Not more susceptible to pests and diseases than other *Heuchera* varieties.

*Environmental stresses.*—Tolerant to heat and humidity.

*Root description.*—Fibrous roots on woody rootstalks.

*Branching habit.*—Basal rosette, with flowering stems arising from rosettes.

*Propagation.*—In vitro propagation is the preferred method, division are also possible.

*Growth rate.*—Vigorous.

Flower stem description:

*Shape.*—Rounded.

*Stem color.*—N199A.

*Stem size.*—An average of 2 mm in diameter and 31.5 cm in length (including rachis).

*Stem strength.*—Strong.

*Stem aspect.*—Flowering stems grow in an average angle of 50° to base (0°=horizontal).

*Stem surface.*—Moderately glossy, densely covered with short hairs an average of 1 mm in length and NN155D in color.

*Stem number.*—Average of 24 flowering stems per 10-liter container.

*Branching.*—Main stem with an average of 3 rosettes.

Foliage description:

*Leaf shape.*—Broad ovate to orbicular.

*Leaf division.*—Simple.

*Leaf base.*—Hastate, touching to slightly overlapping.

*Leaf apex.*—Mucronulate.

*Leaf venation.*—Laciniate.

*Leaf margins.*—Lobed with an average of 7 lobes per leaf, lobe margins crenate.

*Leaf attachment.*—Petiolate.

*Leaf arrangement.*—Alternate, basal rosettes.

*Leaf orientation.*—Typically nearly horizontal to slightly hanging.

*Leaf surface.*—Both surfaces dull and smooth, some sparse pubescence on main veins on underside, hairs average length of 1 mm and NN155D in color.

*Leaf color.*—Young upper surface; 199C, veins and margins N177B, young lower surface; 183D, mature upper surface; color between 153D and 199C, veins 152D with margins a color between 153D and 199C, mature lower surface; 182B.

*Leaf size.*—Average of 10 cm in length and 9.2 cm in width.

*Leaf quantity.*—30 per basal rosette.

*Petioles.*—Round in shape, average of 10.8 cm in length and 1.5 mm in diameter, color is 177B.

*Stipules.*—Small leafy stipules at the base of each leaf, narrow acute apex, with an average of 10 mm in length and 3 mm in width and 70A in color.

Flower description:

*Inflorescence type.*—Numerous small bell-shaped flowers arranged on pyramidal panicles on flower scapes emerging from the base of the rosette.

*Inflorescence size.*—An average of 13.6 cm in height (excluding peduncle) and about 8.6 cm in width.

*Inflorescence number.*—An average of 24 per 10-liter container.

*Flower fragrance.*—None.

*Flower quantity.*—Average of 110 flowers per flowering stem.

*Flower lastingness.*—Average of one week.

*Flower buds.*—Obovate in shape, an average of 5 mm in diameter and 2 mm in diameter, 62A in color, apex 59C in color.

*Flower aspect.*—Drooping to slightly outward.

*Flower type.*—Campanulate.

*Flower size.*—About 7 mm in depth (height) and 6 mm in diameter.

*Petals.*—About 5, rotate arrangement and implanted in the hypanthium at base, oblanceolate in shape, margin is entire, apex is acute, upper and lower surface is dull and smooth, color of upper and lower surface when opening and mature is 58C, about 3 mm in length and 1 mm in width.

*Calyx.*—Campanulate, sepals fused to hypanthium, 7 mm in length and 6 mm in diameter.

*Sepals.*—5, fused, campanulate hypanthium, elliptic in shape, 7 mm in length and 3 mm in width, margin is entire, apex is broadly acute, fused base, both surfaces are dull and moderately covered with very short glandular hairs about 0.1 mm in length and NN155D in color, color: immature upper surface; 68B, immature lower surface; 58C, mature upper surface; 68B, mature lower surface; 58C to 58D.

*Peduncles.*—Primary peduncle (rachis); average of 12.1 cm in length and 1 mm in width, moderate strength, held at a 0° angle (straight on top of flowering stem), color of both surfaces; 183A to 183B, secondary peduncles; average of 1.4 cm in length, 0.75 mm in diameter, moderate in strength, held at a 62.5° (0°=straight upright) to primary peduncle, color of both surfaces; 183A to 183B, surface is glabrous.

*Pedicels.*—Average of 2 mm in length and 0.3 mm in width, moderate in strength, color 183A, pedicel of primary flower of each spikelet straight on top of secondary pedicel, pedicels of secondary and tertiary flowers of each spikelet in an average angle of 45° (0°=straight on top of secondary peduncle), surface is glabrous.

Reproductive organs:

*Gynoecium.*—2 pistils, about 4 mm in length, stigmas pointed in shape, and 21B in color, styles are about 3.5 mm in length and about 155A in color, ovaries between N144B and 8B in color.

*Androcoecium.*—About 5 stamens, anthers are ovate in shape, 0.5 mm and 160D in color, filament 2 mm in length and 58A in color, pollen is moderate in quantity and 12A in color.

*Seed/fruit.*—No fruit or seeds detected to date.

It is claimed:

1. A new and distinct cultivar of hybrid *Heuchera* plant named 'Vulcano' as herein illustrated and described.

* * * * *